(12) United States Patent
Walters et al.

US010807060B2

(10) Patent No.: US 10,807,060 B2
(45) Date of Patent: Oct. 20, 2020

(54) METHOD FOR PREPARING MICROCAPSULES BY DOUBLE EMULSION

(71) Applicant: CALYXIA, Paris (FR)

(72) Inventors: Jamie Walters, Paris (FR); Damien Demoulin, Paris (FR); Jérôme Bibette, Paris (FR)

(73) Assignee: CALYXIA, Paris (FR)

( * ) Notice: Subject to any disclaimer, the term of this patent is extended or adjusted under 35 U.S.C. 154(b) by 197 days.

(21) Appl. No.: 15/759,746

(22) PCT Filed: Sep. 16, 2016

(86) PCT No.: PCT/EP2016/072028
§ 371 (c)(1),
(2) Date: Mar. 13, 2018

(87) PCT Pub. No.: WO2017/046360
PCT Pub. Date: Mar. 23, 2017

(65) Prior Publication Data
US 2018/0185809 A1 Jul. 5, 2018

(30) Foreign Application Priority Data
Sep. 16, 2015 (EP) .................... 15306428

(51) Int. Cl.
*B01F 3/08* (2006.01)
*B01J 13/14* (2006.01)
*C09B 67/02* (2006.01)
*A61K 9/16* (2006.01)
*A01N 25/28* (2006.01)
*C11D 17/00* (2006.01)
*A61K 8/11* (2006.01)
*A23K 40/30* (2016.01)
*A61K 8/87* (2006.01)
*A61Q 19/00* (2006.01)
*B01F 3/22* (2006.01)
*B01F 9/20* (2006.01)
*F28D 20/02* (2006.01)
*B01F 9/00* (2006.01)

(52) U.S. Cl.
CPC .............. *B01J 13/14* (2013.01); *A01N 25/28* (2013.01); *A23K 40/30* (2016.05); *A61K 8/11* (2013.01); *A61K 8/87* (2013.01); *A61K 9/1617* (2013.01); *A61K 9/1635* (2013.01); *A61Q 19/00* (2013.01); *B01F 3/0807* (2013.01); *B01F 3/2292* (2013.01); *B01F 9/20* (2013.01); *C09B 67/0097* (2013.01); *C11D 17/0039* (2013.01); *A61K 2800/10* (2013.01); *A61K 2800/33* (2013.01); *A61K 2800/412* (2013.01); *B01F 2003/0838* (2013.01); *B01F 2009/0083* (2013.01); *F28D 20/023* (2013.01)

(58) Field of Classification Search
CPC .......... A01N 25/28; A23K 40/30; A61K 8/11; A61K 8/87; A61K 9/1617; A61K 9/1635; A61K 2800/10; A61K 2800/33; A61K 2800/412; A61Q 19/00; B01F 3/0807; B01F 3/2292; B01F 9/20; B01F 2003/0838; B01F 2009/0083; B01J 13/14; C09B 67/0097; C11D 17/0039; F28D 20/023; A61P 3/02; A61P 31/02; A61P 31/04

See application file for complete search history.

(56) References Cited

U.S. PATENT DOCUMENTS 5,792,472 A * 8/1998 Roux .................. A61K 9/1277
264/4.1
5,877,145 A 3/1999 Wahl et al.
(Continued)

FOREIGN PATENT DOCUMENTS

CN 101362069 A 2/2009
EP 1033118 A1 9/2000
(Continued)

OTHER PUBLICATIONS

International Search Report dated Nov. 16, 2016 during the prosecution of International Patent Application No. PCT/EP2016/072028.
European Search Report issued in corresponding European Patent Application No. 15 30 6428 dated Feb. 26, 2016 (references cited in EP SR have been previously made of record).

*Primary Examiner* — Irina S Zemel
(74) *Attorney, Agent, or Firm* — Troutman Pepper Hamilton Sanders LLP (57) ABSTRACT

A method for preparing solid microcapsules, comprising the steps of adding under agitation a composition C1 comprising at least one active material to a cross-linkable liquid composition C2, the active material is not an additive to be used in the lubricant, fuel or bitumen industries, drilling sludges or muds, or oil exploration/production, compositions C1 and C2 being immiscible with each other. A first emulsion is obtained comprising droplets of composition C1 dispersed in composition C2, adding under agitation the first emulsion to a liquid composition C3, composition C3 and composition C2 being immiscible with each other, to obtain a second emulsion comprising droplets dispersed in composition C3. Loading the second emulsion in a mixer which applies a homogeneous controlled shear rate to said second emulsion, said shear rate being from 1 000 s-1 to 100 000 s-1, to obtain a third emulsion comprising droplets dispersed in composition C3, and cross-linking the droplets so that solid microcapsules dispersed in composition C3 are obtained.

19 Claims, 3 Drawing Sheets

(56) References Cited

U.S. PATENT DOCUMENTS

| | | |
|---|---|---|
| 5,938,581 A | 8/1999 | Bibette et al. |
| 6,335,315 B1 | 1/2002 | Trinh et al. |
| 2008/0233201 A1 | 9/2008 | Royere et al. |

FOREIGN PATENT DOCUMENTS

| | | |
|---|---|---|
| EP | 2823803 A1 | 1/2015 |
| FR | 2767597 A1 | 2/1999 |
| FR | 2860717 A1 | 4/2005 |
| FR | 2867075 A1 | 9/2005 |
| WO | 03106809 A1 | 12/2003 |

* cited by examiner

METHOD FOR PREPARING MICROCAPSULES BY DOUBLE EMULSION

CROSS-REFERENCE TO RELATED APPLICATIONS

This is a U.S. national phase application under 35 U.S.C. § 371 of International Patent Application No. PCT/EP2016/072028, filed Sep. 16, 2016, and claims benefit of priority to European Patent Application No. 15306428.2, filed Sep. 16, 2015. The entire contents of these applications are hereby incorporated by reference.

FIELD OF TECHNOLOGY

The present invention relates to a method for producing solid microcapsules and to the microcapsules obtained by said method.

BACKGROUND

The problem of isolating an active material from the surrounding environment in order to improve an active material performance is a relatively new area for a number of industries. In most non-bio industries, the losses in performance associated with factors such as hydrolysis, thermal degradation, oxidation and cross-reactivity is addressed by increasing the concentration of the active material to achieve the desired level of performance, which increases the cost, and also introduces further problems associated with the product formed from such unwanted reactions.

However, in a number of industries including chemical, paint, agrochemical industries, it is required to isolate an active material from the surrounding environment, in order to protect the material from hydrolysis, thermal degradation, oxidation, cross-reactivity and other methods which can reduce the performance of the material.

Thus, it is sometimes advantageous to encapsulate an active material in microcapsules.

In addition, many applications require that the thereby produced microcapsules have a small size and/or a narrow size range (i.e. good size monodispersity), in order to have greater control over their overall performance, to improve their dispersion, and to produce more uniform coatings.

In recent years, a large number of encapsulation methods have been developed and reported in the literature, including spray-drying, solvent evaporation, interfacial polymerization, and centrifugal extrusion amongst many others. However, for industrial scale encapsulation methods, emulsification methods, for example batch emulsification methods, dominate because they are able to meet the large volumes needed for industrial demands. Such methods have recourse to a step forming an emulsion of a hydrophobic oil or wax phase, dispersed in an aqueous continuous phase (or alternatively an emulsion of an aqueous phase, dispersed in a hydrophobic oil or wax continuous phase). These two phases are emulsified using either a homogenizer or a stirred vessel equipped with baffles, and they are stabilized using surfactants or emulsifiers. Alternatively, a reaction at the interface between these two phases is used for the formation of a polymer shell.

However, the industrial scale emulsification methods described above produce emulsions, and subsequently microcapsules, which are polydisperse and/or very large (mean size above 10 μm).

Furthermore, said methods require water to form one of the phases described above, and surfactants or emulsifiers to stabilize the emulsion, which may react with the active material encapsulated and/or provide contaminants in each phase, and thus decrease the performances of the active material.

A further limitation of those methods is that, depending upon the viscosity of the emulsion, and the chemical nature of the active material encapsulated, the dimensions of the emulsion droplet, and subsequently the microcapsules, vary significantly.

SUMMARY

The aim of the present invention is thus to provide a method for producing monodisperse microcapsules encapsulating an active material, notably monodisperse microcapsules having a mean size below 5 μm, whilst also having a method in which the dimensions of the microcapsules can be accurately controlled and tuned.

Another aim of the present invention is to provide a method eliminating the requirement of water in the fabrication method, which may negatively impact the active material.

Another aim of the present invention is to provide a method eliminating the requirement of surfactant or emulsifier in the fabrication method, which may negatively impact the active material and its surrounding environment.

Thus, the present invention relates to a method for producing microcapsules, in which independent of the chemical properties of the active material encapsulated in the microcapsules, the microcapsule's diameter, shell thickness, chemical functionality and/or release trigger can be easily tuned to meet the application requirements.

In addition, the present invention relates to method for producing microcapsules, which can be carried out in the absence of water.

In addition, the present invention relates to method for producing microcapsules, which can be carried out in the absence of surfactant and/or emulsifier.

The present invention relates to an industrial scale method for producing monodisperse populations of solid microcapsules, having a mean size preferably below 5 μm, using a double emulsion technique.

DETAILED DESCRIPTION

An object of the present invention is thus a method for preparing solid microcapsules, comprising the steps of:
  a) adding under agitation a composition C1 comprising at least one active material to a cross-linkable liquid composition C2, wherein the active material is not an additive to be used in the lubricant, fuel or bitumen industries, or in drilling sludges or muds, or an additive to be used in oil exploration/production, composition C1 and composition C2 being immiscible with each other, so that a first emulsion is obtained, said first emulsion comprising droplets of composition C1 dispersed in composition C2, b) adding under agitation the first emulsion obtained in step a) to a liquid composition C3, composition C3 and composition C2 being immiscible with each other, so that a second emulsion is obtained, said second emulsion comprising droplets dispersed in composition C3, c) loading the second emulsion obtained in step b) in a mixer which applies a homogeneous controlled shear rate to said second emulsion, said shear rate being from 1 000 s' to 100 000 s$^{-1}$, so that a third emulsion is obtained, said third emulsion comprising droplets dispersed in composition C3, and d) cross-linking the droplets obtained in step c), so that solid microcapsules dispersed in composition C3 are obtained.

The method of the invention implements a homogeneous controlled high shear (over 1 000 s$^{-1}$) mixing step that uniformly subjects the droplets of the second emulsion to a high shear rate y, which fragments the polydisperse population droplets of the second emulsion into a monodisperse population of double droplets (third emulsion).

The middle phase of the third emulsion (composition C2) is then polymerized to form a solid shell, minimizing any coalescence and growth.

The present invention solves a double emulsion method to create microcapsules, which can be prepared in the absence of water, surfactant and/or emulsifier, which may negatively interact with the active material encapsulated and/or induce contaminants into the surrounding media (composition C3).

The method of the invention may be a continuous or a batch method for preparing solid microcapsules.

According to one embodiment, the method of the invention is a batch method.

Step a)

During step a), a composition C1 is added to a cross-linkable liquid composition C2, said addition being carried out under agitation, meaning that the composition C2 is stirred, typically mechanically, while composition C1 is added, in order to emulsify the mixture of composition C1 and composition C2.

The addition of composition C1 to composition C2 is typically carried out dropwise.

During step a), composition C1 is at a temperature between 0° C. and 100° C., preferably between 10° C. and 80° C. and most preferentially from 15° C. to 60° C. During step a), composition C2 is at a temperature between 0° C. and 100° C., preferably between 10° C. and 80° C. and most preferentially from 15° C. to 60° C.

In the conditions of the addition of step a), composition C1 and composition C2 are immiscible with each other, which means that the amount (in mass) of composition C1 able to be solubilized in composition C2 is less than or equal to 5%, preferably 1%, preferentially 0.5%, relative to the total mass of composition C2, and that the amount (in mass) of composition C2 able to be solubilized in composition C1 is less than or equal to 5%, preferably 1%, preferentially 0.5%, relative to the total mass of composition C1.

Thus, when it enters in contact with composition C2 under agitation, composition C1 is dispersed in the form of droplets (also called single droplets).

The immiscibility between composition C1 and composition C2 also prevents the active material to migrate from composition C1 to composition C2.

Upon addition of composition C1, composition C2 is stirred in order to form a liquid/liquid emulsion (also called first emulsion, or C1-in-C2 emulsion, or C1/C2 emulsion) comprising droplets of composition C1 (single droplets) dispersed in composition C2.

Figure 1:
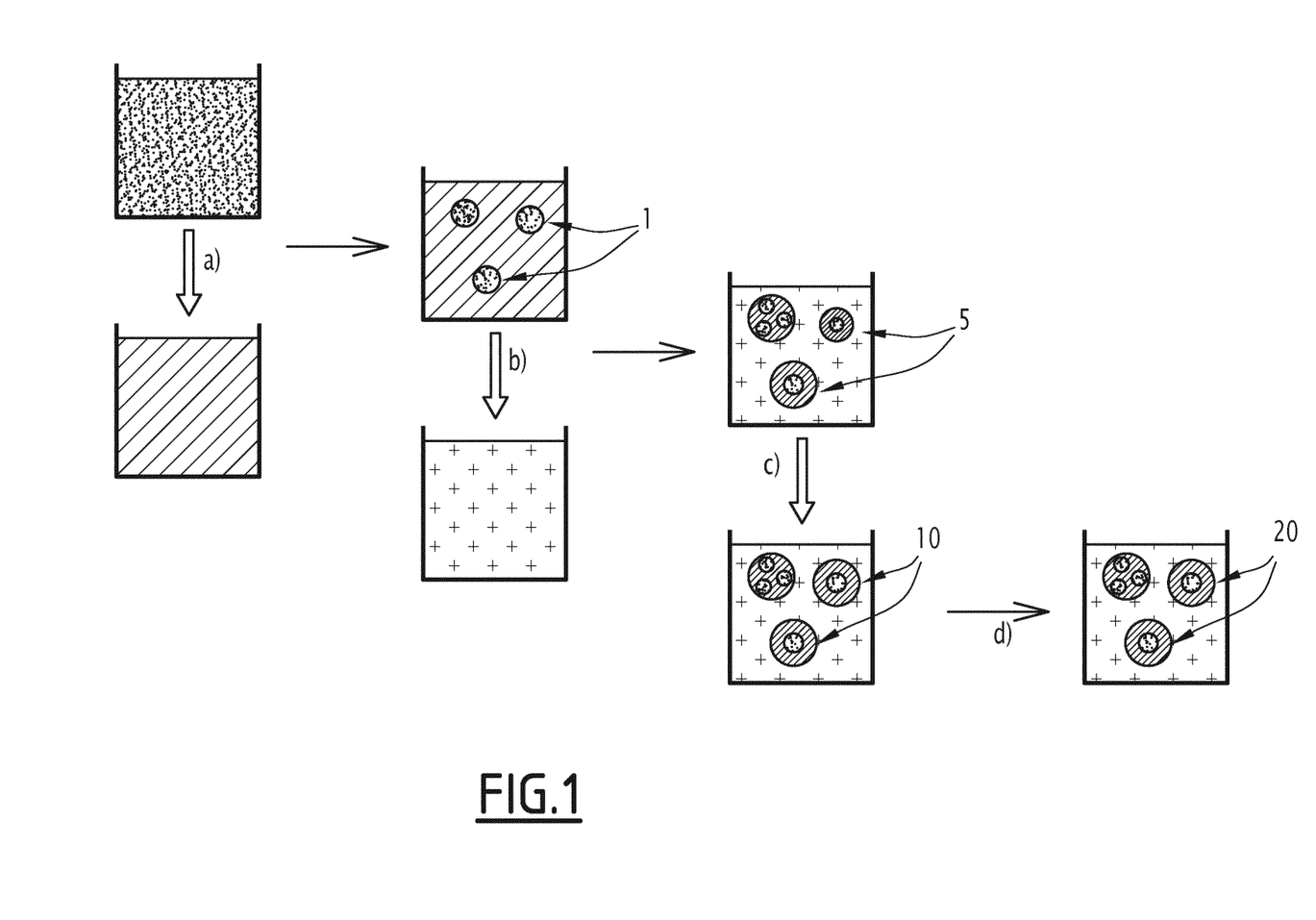
FIG. 1 schematically represents the method of the invention.

FIG. 1 schematically represents the method of the invention and notably schematically represents droplets 1 obtained in step a), by adding composition C1 to composition C2.

In order to implement step a), any type of agitator usually used for making emulsions can be used, such as overhead stirrer (speed of mixing from 100 rpm to 2 000 rpm), rotor-stator mixer (speed of mixing from 100 rpm to 5 000 rpm), or colloidal mill (speed of mixing from 1 000 rpm to 10 000 rpm). Alternatively, ultrasound homogenizer, membrane homogenizer or high pressure homogenizer can also be used.

Composition C1 comprises at least one active material, which is not an additive to be used in the lubricant, fuel or bitumen industries, or in drilling sludges or muds, or an additive to be used in oil exploration/production.

According to one embodiment of the invention, composition C1 is a monophasic liquid composition, meaning that the active material is in a pure form or is solubilized into composition C1.

According to a variant of this embodiment, the active material is solubilized into composition C1.

According to this variant, composition C1 may consist of a solution of the active material in an organic solvent, or a mixture of organic solvents.

According to this variant, composition C1 may also consist of a solution of the active material in an aqueous phase, which comprises water and eventually hydrophilic organic solvents.

According to this embodiment, the content of the active material in composition C1 is typically comprised from 1% to 99%, preferably from 5% to 95%, preferentially from 10% to 90%, from 20% to 80%, from 30% to 70%, or from 40% to 60%, by weight relative to the total weight of composition C1.

According to another variant of this embodiment, the active material is present in a pure form in composition C1, meaning that composition C1 consists of the active material.

According to another embodiment of the invention, composition C1 is a biphasic composition, meaning that the active material is dispersed, either in a liquid form or in a solid form, into the composition C1 and is not totally solubilized into composition C1.

According to a variant of said embodiment, the active material is dispersed in the form of solid particles into composition C1.

According to this variant, composition C1 may consist of a dispersion of solid particles of the active material in an organic solvent, or a mixture of organic solvents.

According to this variant, composition C1 may also consist of a dispersion of solid particles of the active material in an aqueous phase, which comprises water and eventually hydrophilic organic solvents.

According to another variant of this embodiment, the active material is dispersed in the form of liquid droplets into composition C1.

According to this variant, composition C1 may consist of an emulsion of droplets of the active material dispersed in an organic solvent, or a mixture of organic solvents.

According to this variant, composition C1 may also consist of an emulsion of droplets of the active material dispersed in an aqueous phase, which comprises water and eventually hydrophilic organic solvents.

According to this embodiment, the content of the active material in composition C1 is typically comprised from 1% to 99%, preferably from 5% to 95%, preferentially from 10% to 90%, from 20% to 80%, from 30% to 70%, or from 40% to 60%, by weight relative to the total weight of composition C1.

When the active material is in the form of particles in composition C1, it is preferably in the form of nanoparticles, either spherical or non-spherical, which may have a size ranging from 1 nm to 1 000 nm.

According to one embodiment, the active material is selected from the group consisting of:

- cross-linkers, hardeners, organic catalysts and metal-based catalysts (for example organo-complexes and inorgano-complexes of platinum, palladium, titanium, molybdenum, copper, or zinc) for polymerization of elastomer formulations, rubber formulations, paint formulations, coating formulations, adhesive formulations, or sealant formulations;
- dyes, colorants, pigments for inks, personal care products, elastomer formulations, rubber formulations, paint formulations, coating formulations, adhesive formulations, sealant formulations, or paper formulations;
- fragrances for detergents, housecleaning products, personal care products, textiles (so-called smart textiles), coating formulations. Fragrances useful to the invention are any of the compounds belonging to the list of standards published and updated by the International Fragrance Association (IFRA);
- aromas, flavors, vitamins, aminoacids, proteins, essential lipids, probiotics, antioxidants, preservatives for feed and food products;
- fabric softeners and conditioners for detergents and personal care products. Compounds useful to the invention include but are not limited to these enumerated in U.S. Pat. Nos. 6,335,315 and 5,877,145;
- bioactive compounds such as enzymes, vitamins, proteins, vegetable extracts, moisturizers, sanitizers, antibacterial agents, sunscreen agents, drugs, for personal care products, textiles (so-called smart textiles). These compounds include but are not limited to vitamin A, vitamin B, vitamin C, vitamin D, vitamin E, para aminobenzoic acid, alpha hydroxyacid, camphor, ceramides, ellagic acid, glycerin, glycin, glycolic acid, hyaluronic acid, hydroquinone, isopropyl, isostearate, isopropyl palmitate, oxybenzone, panthenol, proline, retinol, retinyl palmitate, salicylic acid, sorbic acid, sorbitol, triclosan, tyrosine; and
- fertilizers, herbicides, insecticides, pesticides, fungicides, repellants, and disinfectants for agrochemicals.

Insecticides useful to the invention include but are not limited to:

O,O-diethyl O-2-isopropyl-6-methylpyrimidin-4-yl phosphorothioate,
O,O-diethyl S-2-ethylthioethyl phosphorodithioate,
S-chloromethyl O,O-diethyl phosphorodithioate,
O-ethyl S,S-dipropyl phosphorodithioate,
O,O-diethyl S-ethylthiomethyl phosphorodithioate,
S-tertiobutylthiomethyl O,O-diethyl phosphorodithioate,
O,O-diethyl-O-4-methylsulphinylphenyl phosphorothioate,
O-(4-bromo-2-chlorophenyl) O-ethyl-S-propyl phosphorodithioate,
S-1,2-di(ethoxycarbonyl)ethyl O,O-dimethylphosphorodithioate,
O,O,O',O'-tetraethyl-S,S'-methylene di(phosphorodithioate),
O-(4-bromo-2,5-dichlorophenyl) O,O-diethyl phosphorothioate,
S-4-chlorophenylthiomethyl O,O-diethyl phosphorodithioate,
O-2,5-dichloro-4-(methylthio)phenyl O,O-diethyl phosphorodithioate,
O-4-cyanophenyl O,O-dimethyl phosphorothioate,
O,O-dimethyl O-2-methylthioethyl phosphorothioate,
O,O-diethyl O-2-ethylthioethyl phosphorothioate,
O-2,4-dichlorophenyl O,O-diethyl phosphorothioate,
O-2,4-dichlorophenyl O-ethyl phenylphosphorothioate,
1,3-di(methoxycarbonyl)-1-propen-2-yldimethyl phosphate,
2-chloro-1-(2,4-dichlorophenyl)vinyl diethyl phosphate,
O,O-dimethyl-O-4-nitro-m-tolyl phosphorothioate,
O,O-dimethyl-O-4-methylthio-m-tolyl phosphorothioate,
0-(5-chloro-1-isopropyl-1,2,4-triazol-3-yl) O,O-diethyl-phosphorothioate,
S-2-isopropylthioethyl O,O-dimethyl phosphorodithioate,
4-(methylthio)phenyl dipropylphosphate,
1,2-dibromo-2,2-dichloroethyl dimethylphosphate,
O,O-diethyl-alpha-cyanobenzylidene amino-oxyphosphorothioate,
O,O-diethyl O-4-nitrophenyl phosphorothioate,
O-2-diethylamino-6-methylpyrimidin-4-yl O,O-diethyl phosphorothioate,
O-2-diethylamino-6-methylpyrimidin-4-yl O,O-dimethyl phosphorothioate,
O,O,O',O'-tetraethyldithiopyrophosphate,
O,O,O',O'-tetramethyl-O,O'-thiodi-p-phenylenediphosphorothioate,
S,S'-(1,4-dioxane-2,3-diyl) O,O,O',O'-tetraethyl di(phosphorodithioate),
S-2-ethylthioethyl-O,O-dimethylphosphorodithioate,
3-phenoxybenzyl-(+−)-cis-transchrysanthemate,
pyrethrins-2-(2-butoxyethoxy)erhylthiocyanate isobornylthiocyanoacetate,
carbon disulfide 2-(4-tertio-butylphenoxy)cyclohexyl prop-2-ynyl sulphite,
4-6-dinitro-6-octylphenylcrotonates,
ethyl 4,4'-dichlorobenzilate,
O,O-diethyl-O-1-phenyl-1,2,4-triazol-3-ylphosphorothioate,
O-ethyl O-2,4,5-trichlorophenyl ethylphosphonothioate,
(++3-allyl-2-methyl-4-oxocyclopent-2-enyl-(+)-cis,trans-chrysanthemate, and
(++3-allyl-2-methyl-4-oxocyclopent-2-enyl-(+)-trans-chrysanthemate.

Fungicides useful to the invention include but are not limited to:

copper naphthenate,
5-ethoxy-3-trichloromethyl-1,2,4-thiadiazole, and
O-ethyl S,S-diphenyl phosphorodithioate.

Repellants useful to the invention include but are not limited to:

6-butoxycarbonyl-2,3-dihydro-2,2-dimethylpyran-4-one,
N,N-diethyl-m-toluamide,
dibutylphthalate dibutylsuccinate,
1,5a,6,9,9a,9b-hexahydro-4a(4H)-dibenzofurancarboxaldehyde, and
dipropylpyridine-2,5-dicarboxylate.

Herbicides useful to the invention include but are not limited to:

2-(1,2-dimethylpropylamino)-4-ethyl-amino-6-methylthio-1,3,5-triazine-2-ethyl-5-methyl-5-(2-methylbenzyloxy)-1,3-dioxane,
S-ethyl-N-cyclohexyl-N-ethylthiocarbamate,
S-2,3-dichloroallyl di-isopropylthiocarbamate,
S-propyl butylethylthiocarbaxate,
S-2,3,3-trichloroallyl diisopropylthiocarbamate,
S-ethyl dipropylthiocarbamate,
S-4-chlorobenzyl diethylthiocarbamate,
S-ethyl diisobutylthiocarbamate,
S-benzyl di-secbutylthiocarbamate,
S-propyl dipropylthiocarbamate,
S-ethylhexahydro-1H-azepine-1-carbothioate,
N,N-diallylchloroacetamide,
N-butoxymethyl-alpha-chloro-2',6'-diethylacetanilide,
S—(O,O-diisopropyl phosphorodithioate) ester of N-(2-mercaptoethyl)benzenesulfonarnide,
alpha-chloro-6'-ethyl N-(2-methoxy-1-methylethyl)-acetamide,
N-benzyl N-isopropyltrimethylacetamide, and
2-chloroallyl diethyldithiocarbamate.

The active material may also be an active known in the art as Phase Change Material (PCM) able to absorb and release heat upon phase change, for energy storage materials.

PCM and their applications are described for instance in "A review on phase change energy storage: materials and applications", Farid et al., Energy Conversion and Management, 2004, 45 (9-10), 1597-1615.

Examples of PCM include but are not limited to: molten salts of aluminum phosphate, ammonium carbonate, ammonium chloride, caesium carbonate, caesium sulfate, calcium citrate, calcium chloride, calcium hydroxide, calcium oxide, calcium phosphate, calcium saccharate, calcium sulfate, cerium phosphaten iron phosphaten lithium carbonate, lithium sulfate, magnesium chloride, magnesium sulfate, manganese chloride, manganese nitrate, manganese sulfate, potassium acetate, potassium carbonate, potassium chloride, potassium phosphate, rubidium carbonate, rubidium sulfate, disodium tetraborate, sodium acetate, sodium bicarbonate, sodium bisulfate, sodium citrate, sodium chloride, sodium hydroxide, sodium nitrate, sodium percarbonate, sodium persulfate, sodium phosphate, sodium propionate, sodium selenite, sodium silicate, sodium sulfate, sodium tellurate, sodium thiosulfate, strontium hydrophosphate, zinc acetate, zinc chloride, sodium thiosulfate, and mixtures thereof; organic compounds such as saturated paraffinic hydrocarbons, polyethylene glycols, waxes and mixtures thereof.

The active material may also be selected from waste materials defined as dangerous, toxic or harmful to mankind or to the environment and as such require total confinement for handling and storage.

Examples of such waste materials include but are not limited to toxic heavy metals, and radioactive compounds.

Composition C2 is a cross-linkable liquid composition, meaning that it is a composition able to polymerize (cross-link) to yield a solid material, which will from the polymerized shell of the solid microcapsules of the invention.

Composition C2 is typically a prepolymer formulation able to polymerize into a solid material.

According to one embodiment of the invention, composition C2 comprises at least one monomer or polymer, at least one cross-linker and at least one initiator of polymerization.

According to this embodiment, composition C2 comprises typically from 50% to 95% by weight of monomer or polymer, or mixture of monomers or polymers, relative to the total weight of composition C2.

According to this embodiment, composition C2 comprises typically from 1% to 20% by weight of cross-linker or mixture of cross-linkers, relative to the total weight of composition C2.

According to this embodiment, composition C2 comprises typically from 0.1% to 5% by weight of initiator or mixture of initiators, relative to the total weight of composition C2.

By "monomer or polymer", it should be understood any building block suitable for forming a solid material by polymerization, either alone or in combination with others monomers or polymers.

The monomers may be selected from monomers bearing at least one reactive function selected from the group consisting of acrylate; methacrylate; vinyl ether; N-vinyl ether; mercaptoester; thiolen; siloxane; epoxy; oxetan; urethane; isocyanate; and peroxide.

Notably, the monomers may be selected from monomers bearing at least one of the above reactive functions and additionally bearing one or more functions selected from the group consisting of primary, secondary, and tertiary alkylamine; quaternary amine; sulfate; sulfonate; phosphate; phosphonate; hydroxyl; carboxylate; and halogen.

The polymers may be selected from polyethers, polyesters, polyurethanes, polyureas, polyethylene glycols, polypropylene glycols, polyamides, polyacetals, polyimides, polyolefins, polysulfides, and polydimethylsiloxanes, said polymers bearing at least one reactive function selected from the group consisting of acrylate; methacrylate; vinyl ether; N-vinyl ether; mercaptoester; thiolen; siloxane; epoxy; oxetan; urethane; isocyanate; and peroxide.

Examples of such polymers include but are not limited to: 2-(1-naphthyloxy)-ethyl acrylate, 2-(2-naphthyloxy)-ethyl acrylate, 2-(2-naphthyloxy)-ethyl methacrylate, sorbitol dimethacrylate, acrylamide, 2-propeneamide, 2-(1-naphthyloxy) ethanol, 2-(2-naphthyloxy) ethanol, 1-chloro-2,3-epoxypropane, poly(n-butyl isocyanate), poly(N-vinyl carbazole), poly(N-vinyl pyrrolidone), poly(p-benzamide), poly(p-chlorostyrene), poly(p-methyl styrene), poly(p-phenylene oxide), poly(p-phenylene sulfide), N-(methacryloxyethyl)succinimide, polybenzimidazol, polybutadiene, butylene terephthalate, polychloral, polychloro trifluoro ethylene, polyether imide, polyether ketone, polyether sulfone, polyhydridosilsesquioxane, poly(m-phenylene isophthalamide), methyl 2-acrylamido-2-methoxyacetate, 2-acrylamido-2-methylpropanesulfonic acid, mono-butyl maleate, butylmethacrylate, N-tert-butylmethacrylamide, N-n-butylmethacrylamide, cyclohexylmethacrylamide, m-xylenebisacrylamide 2,3-dimethyl-1,3-butadiene, N,N-dimethylmethacrylamide, n-butyl methacrylate, cyclohexyl methacrylate, isobutyl methacrylate, 4-cyclohexylstyrene, cyclol acrylate, cyclol methacrylate, diethyl ethoxymethylenemalonate, 2,2,2-trifluoroethyl methacrylate, 1,1,1-trimethylolpropane trimethacrylate, methacrylate, N,N-dimethylanilin, dihydrazide, isophthalic dihydrazine, isophthalic acid, dimethyl benzilketal, epichlorohydrin, ethyl-3,3-diethoxyacrylate, ethyl-3,3-dimethylacrylate, ethyl vinylketone, vinyl ethylketone, penten-3-one, formaldehyde diallyl acetal, fumaronitrile, glyceryl propoxy triacrylate, glyceryl trimethacrylale, glycidoxypropyltrimethoxysilane, glycidyl acrylate, n-heptyl acrylate, acrylic acid n-heptyl ester, n-heptyl methacrylate, 3-hydroxypropionitrile, 2-hydroxypropyl acrylate, 2-hydroxypropyl methacrylate, N-(methacryloxyethyl)phthalimide, 1,9-nonanediol diacrylate, 1,9-nonanediol dimethacrylate, N-(n-propyl) acrylamide, orthophthalic acid, isophthalic acid, 1,4-benzenedicarboxylic acid, 1,3-benzenedicarboxylic acid, phthalic acid, mono-2-acryloxyethyl ester, terephthalic acid, phthalic anhydride, polyethylene glycol diacrylate, polyethylene glycol methacrylate, polyethylene glycol dimethacrylate, isopropyl acrylate, sorbitol pentaacrylate, vinyl bromoacetate, polychloroprene, poly(di-n-hexyl silylene), poly(di-n-propyl siloxane), polydimethyl silylene, polydiphenyl siloxane, vinyl propionate, vinyl triacetoxysilane, vinyl tris-tert-butoxysilane, vinyl butyral, vinyl alcohol, vinyl acetate, ethylene co-vinyl acetate, bisphenol-A polysulfone, 1,3-dioxepane, 1,3-dioxolane, 1,4-phenylene vinylene, poly(2,6-dimethyl-1A-phenylene oxide), poly(4-hydroxy benzoic acid), poly(4-methyl pentene-1), poly(4-vinyl pyridine), polymethylacrylonitrile, polymethylphenylsiloxane, polymethylsilmethylene, polymethylsilsesquioxane, poly(phenylsilsesquioxane), poly(pyromellitimide-1.4-diphenyl ether), tetrahydrofuran, polythiophene, poly(trimethylene oxide), polyacrylonitrile, ether sulphone, ethylene-co-vinyl acetate, perfluor ethylen propylene, poly(perfluoralkoxyl alkan), poly(styrene-acrylonitrile).

By "cross-linker", it should be understood any compound carrying at least two reactive functions suitable for cross-linking a monomer or a polymer, or a mixture of monomers or polymers, when polymerized.

The cross-linker may be selected from molecules bearing at least two functions selected from the group consisting of acrylate; methacrylate; vinyl ether; N-vinyl ether; mercaptoester; thiolen; siloxane; epoxy; oxetan; urethane; isocyanate; and peroxide.

By "initiator", it should be understood any compound able to fragment when it is excited by a source of energy.

Preferably, composition C2 is a photocross-linkable liquid composition and the initiator is thus a photoinitiator for polymerization.

The initiator may be selected from the group consisting of:
α-hydroxyketones, such as 2-hydroxy-2-methyl-1-phenyl-1-propanone;
α-aminoketones, such as 2-benzyl-2-dimethylamino-1-(4-morpholinophenyl)-butanone-1;
α-dicarbonyl derivatives, such as benzildimethyl ketal;
acylphosphine oxides, such as bis-acylphosphine oxide;
aromatic ketones, such as benzophenone;
phenylglyoxylates, such as phenyl glyoxylic acid methyl ester;
oxime esters, such as [1-(4-phenylsulfanylbenzoyl)heptylideneamino]benzoate;
sulfonium salts,
iodonium salts, and
oxime sulfonates.

According to a variant of the invention, composition C2 may also comprise an additional monomer or polymer able to enhance the properties of the microcapsules shell and/or to impart the microcapsules shell with new properties, such as to make the microcapsules shell responsive to an external trigger.

Such an additional monomer or polymer may be a monomer or polymer bearing a pH-sensitive group, a temperature-sensitive group, a UV-sensitive group or IR-sensitive group.

These additional monomers or polymers may induce the rupture of the solid microcapsules and the subsequent release of their content, when stimulated by a pH, a temperature, a UV or a IR external trigger.

The additional monomer or polymer may be selected from the monomers or polymers bearing at least one reactive function selected from the group consisting of acrylate; methacrylate; vinyl ether; N-vinyl ether; mercaptoester; thiolen; siloxane; epoxy; oxetan; urethane; isocyanate; and peroxide; and also bearing any one of the following groups:
a hydrophobic group such as a fluorinated group, for instance trifluoroethyl methacrylate, trifluoroethyl acrylate, tetrafluoropropyl methacrylate, pentafluoropropyl acrylate, hexafluorobutyl acrylate, or fluorophenyl isocyanate;
a pH-sensitive group such as primary, secondary or tertiary amine, carboxylic acid, phosphate, sulfate, nitrate, or carbonate;
a UV-sensitive or UV-cleavable group (also called photochromic group) such as azobenzene, spiropyran, 2-diazo-1,2-naphthoquinone, o-nitrobenzyl, thiol, or 6-nitro-veratroyloxycarbonyl, for instance poly(ethylene oxide)-block-poly(2-nitrobenzylmethacrylate), and other block copolymers, as described for instance in Liu et al., Polymer Chemistry 2013, 4, 3431-3443;
an IR-sensitive or IR-cleavable group such as o-nitrobenzyl or 2-diazo-1,2-naphthoquinone, for instance polymers described in Liu et al., Polymer Chemistry 2013, 4, 3431-3443; and
a temperature sensitive group such as poly(N-isopropylacrylamide).

Alternatively, composition C2 may also comprise nanoparticles bearing on their surface at least one reactive function selected from the group consisting of acrylate; methacrylate; vinyl ether; N-vinyl ether; mercaptoester; thiolen; siloxane; epoxy; oxetan; urethane; isocyanate; and peroxide. These nanoparticles may generate heat when stimulated by an external electromagnetic field, inducing the rupture of the solid microcapsules and the subsequent release of their content.

Suitable nanoparticles may be selected from gold, silver, and titanium dioxide nanoparticles (which react to an IR field) and iron oxide nanoparticles (which react to a magnetic field).

According to one embodiment, the viscosity of composition C2 at 25° C. is from 500 mPa·s to 100 000 mPa·s.

Preferably, the viscosity of composition C2 at 25° C. is from 1 000 mPa·s to 50 000 mPa·s, preferentially from 5 000 mPa·s to 25 000 mPa·s, for example from 10 000 mPa·s to 20 000 mPa·s.

Preferably, the viscosity of composition C2 is higher than the viscosity of composition C1.

According to this embodiment, independent of the active material viscosity or chemical properties, the kinetic destabilization of the droplets of first emulsion is significantly slow, which enables the shell of the microcapsules to be polymerized during step d), providing thermodynamic stabilization before kinetic destabilization can arise.

Thus, the relatively high viscosity of composition C2 ensures the stability of the first emulsion obtained in step a).

This embodiment solves the limitation associated with large variance in microcapsule properties that usually occurs when varying the active material for encapsulation.

Preferably, there is a low interfacial tension between composition C1 and composition C2. Suitable interfacial tensions typically range from 0 mN/m to 50 mN/m, preferably from 0 mN/m to 20 mN/m.

The low interfacial tension between composition C1 and composition C2 also advantageously ensures the stability of the first emulsion obtained in step a).

According to one embodiment, the volume of composition C1 to the volume of composition C2 ratio is from 1:10 to 10:1.

Preferably, said ratio is from 1:3 to 5:1, preferentially from 1:2 to 4:1.

Said ratio can be tailored according to these ranges in order to control the thickness of the resulting microcapsule polymerized shell.

Step b)

During step b), the first emulsion obtained in step a) is added to a liquid composition C3, said addition being carried out under agitation, meaning that the composition C3 is stirred, typically mechanically, while the first emulsion is added, in order to emulsify the mixture of composition C1, composition C2, and composition C3.

The addition of the first emulsion to composition C3 is typically carried out dropwise.

During step b), the first emulsion is at a temperature typically comprised from 15° C. to 30° C. During step b), composition C3 is at a temperature typically comprised from 15° C. to 30° C.

In the conditions of the addition of step b), composition C2 and composition C3 are immiscible with each other, which means that the amount (in mass) of composition C2 able to be solubilized in composition C3 is less than or equal to 5%, preferably 1%, preferentially 0.5%, relative to the total mass of composition C3, and that the amount (in mass) of composition C3 able to be solubilized in composition C2 is less than or equal to 5%, preferably 1%, preferentially 0.5%, relative to the total mass of composition C2.

Thus, when it enters in contact with composition C3 under agitation, the first emulsion (C1-in-C2 or C1/C2) is dispersed in the form of droplets (also called double droplets), the dispersion of these droplets of first emulsion in the continuous phase C3 being called the second emulsion.

Typically, a double droplet formed during step b) corresponds to a single droplet of composition C1 as described above, surrounded by a shell of composition C2 which encapsulates totally said single droplet.

The double droplet formed during step b) may also comprise at least two single droplets of composition C1 as described above, said single droplets being surrounded by one shell of composition C2 which encapsulates totally said single droplets.

Thus, said double droplets comprise a core consisting of one or more single droplets of composition C1, and a layer of composition C2 surrounding said core.

The resulting second emulsion is generally a polydisperse double emulsion (C1-in-C2-in-C3 emulsion or C1/C2/C3 emulsion), meaning that the double droplets do not have a sharp distribution of size in said second emulsion.

FIG. 1 schematically represents the method of the invention and notably schematically represents polydisperse droplets 5 obtained in step b), by adding into composition C3 the first emulsion of droplets 1 dispersed in composition C2.

The immiscibility of composition C2 with composition C3 prevents the layer of composition C2 to mix with composition C3 and thus assures the stability of the second emulsion.

The immiscibility of composition C2 with composition C3 also prevents the active material in composition C1 to migrate from the core of the droplets to composition C3.

In order to implement step b), any type of agitator usually used for making emulsions can be used, such as overhead stirrer (speed of mixing 100 to 2 000 rpm), rotor-stator mixer (speed of mixing 100 to 5 000 rpm), or colloidal mill (speed of mixing 1 000 to 10 000 rpm). Alternatively, ultrasound homogenizer, membrane homogenizer or high pressure homogenizer can also be used.

According to one embodiment, composition C3 is a hydrophobic phase.

According to said embodiment, composition C3 typically comprises an elastomer or resin formulation, a paint, a coating, a sealant, an adhesive, or a hydrocarbon oil (such as paraffinic oil, naphthenic oil, vegetable oil, mineral oil, castor oil, corn oil, peanut oil, jojoba oil, alkyl adipates, alkyl palmitates, alkyl oxystearates oils, glycerol triacetates, or isopropyl myristates).

According to another embodiment, composition C3 is a hydrophilic phase.

According to said embodiment, composition C3 is typically an aqueous composition comprising a thickening agent, such as dextran, alginate, cellulose and cellulose derivatives (such as methylcellulose, ethylcellulose, hydroxyethylcellulose, hydroxypropylcellulose, cetyl hydroxyethylcellulose), guar gum, xanthan gum, gelatin, starch, agar, carrageenan hydrolyzed collagen, hyaluronic acid, pectin, acrylate polymers and copolymers, polyacrylic acid, carbomer, polyacrylamide, polyvinylpyrrolidone, or polyvinyl acetate.

According to one embodiment, the viscosity of composition C3 at 25° C. is higher than the viscosity at 25° C. of the first emulsion obtained in step a).

Composition C3 has typically a viscosity at 25° C. from 500 mPa·s to 100 000 mPa·s.

Preferably, the viscosity of composition C3 at 25° C. is from 1 000 mPa·s to 50 000 mPa·s, preferentially from 5 000 mPa·s to 25 000 mPa·s, for example from 10 000 mPa·s to 20 000 mPa·s.

According to this embodiment, given the higher viscosity of the continuous phase (composition C3) compared to the first emulsion, the kinetic destabilization of the double droplets (second emulsion) is significantly slow, providing thermodynamic stabilization before kinetic destabilization can arise.

Thus, the relatively high viscosity of composition C3 ensures the stability of the second emulsion obtained in step b).

Preferably, there is a low interfacial tension between composition C2 and composition C3.

The low interfacial tension between composition C2 and composition C3 also ensures the stability of the second emulsion obtained in step b).

According to one embodiment, during step b), the volume of the first emulsion to the volume of composition C3 ratio is from 1:10 to 10:1.

Preferably, said ratio is from 1:9 to 3:1, preferentially from 1:8 to 1:1, for example from 1:6 to 1:2.

Said ratio can be tailored according to these ranges in order to control the overall content of encapsulated active material in the resulting population of polymerized microcapsules.

Step c)

In step c), the second emulsion obtained in step b), consisting of polydisperse droplets dispersed in a continuous phase, is sheared in a mixer, which applies a homogeneous controlled shear rate, comprised from 1 000 to 100 000 s$^{-1}$.

Surprisingly, the inventors have found that this emulsification process creates, through a fragmentation mechanism, a double emulsion with improved size variance, i.e. a double emulsion consisting of monodisperse double droplets (also called third emulsion).

In a mixing device, the shear rate is said to be homogeneous and controlled when, irrespective of the variation in the time of the shear rate, it passes through a maximum value which is the same for all parts of the emulsion, at a given instant which can differ from one point in the emulsion to another. The exact configuration of the mixing device is not essential according to the invention provided that, on leaving this device, the entire emulsion has been subjected to the same maximum shear. Suitable mixers for carrying out step c) are notably described in U.S. Pat. No. 5,938,581.

The second emulsion can undergo homogeneous controlled shear when circulated through a cell formed by:
two concentric rotating cylinders (also called Couette-geometry mixer),
two parallel rotating discs, or
two parallel oscillating plates.

The shear rate applied to the second emulsion is comprised from $1\,000\,s^{-1}$ to $100\,000\,s^{-1}$, preferably from $1\,000\,s^{-1}$ to $50\,000\,s^{-1}$, preferentially from $2\,000\,s^{-1}$ to $20\,000\,s^{-1}$.

During step c), the second emulsion is introduced in the mixer and is then submitted to a shear stress which results in the formation of a third emulsion. Said third emulsion is chemically the same as the second emulsion, but it consists in monodisperse double droplets, whereas the second emulsion consisted in polydisperse double droplets. The third emulsion typically consists of a dispersion of double droplets comprising a core consisting of one or more single droplets of composition C1, and a layer of composition C2 surrounding said core, said double droplets being dispersed in composition C3.

The difference between the second emulsion and the third emulsion is the variance in size of the double droplets: the droplets of the second emulsion are polydisperse in size whereas the droplets of the third emulsion are monodisperse, thanks to the fragmentation mechanism described above.

Preferably, the second emulsion is introduced in the mixer continuously, meaning that the amount of double emulsion introduced at the inlet of the mixer is the same as the amount of third emulsion outgoing from the outlet of the mixer.

Since the size of the droplets of the third emulsion subsequently corresponds to the size of the solid microcapsules after polymerization, it is possible to tune the microcapsule size and shell thickness by adjusting the shear rate during step c), with a strong correlation between decreasing droplet size and increasing shear rate.

This allows the resultant dimensions of the microcapsules to be tailored by varying the shear rate applied during step c).

According to a preferred embodiment, the mixer implemented in step c) is a Couette-geometry mixer, comprising two concentric cylinders, an outer cylinder of inner radius $R_o$ and an inner cylinder of outer radius $R_i$, the outer cylinder being fixed and the inner cylinder being rotating with an angular velocity $\omega$.

A Couette-geometry mixer suitable for the method of the invention may be purchased from T.S.R. Company France.

According to one embodiment, the angular velocity $\omega$ of the rotating inner cylinder of the Couette-geometry mixer is over than or equals to $30\,rad\cdot s^{-1}$.

For example, the angular velocity $\omega$ of the rotating inner cylinder is about $70\,rad\cdot s^{-1}$.

The dimensions of the fixed outer cylinder of the Couette-geometry mixer can be chosen to modulate the gap ($d=R_o-R_i$) between the rotating inner cylinder and the fixed outer cylinder.

According to one embodiment, the gap $d=R_o-R_i$ between the two concentric cylinders of the Couette-geometry mixer is from 50 µm to 1 000 µm, preferably from 100 µm to 500 µm, for example from 200 µm to 400 µm.

For example, the gap d between the two concentric cylinders is 100 µm.

According to the embodiment of the invention implementing a Couette-geometry mixer, during step c), the second emulsion is introduced at the inlet of the mixer, typically via a pump, and is directed to the gap between the two concentric cylinders, the outer cylinder being fixed and the inner cylinder been rotating at an angular velocity $\omega$.

The second emulsion is thus submitted to a shear stress which results in the formation of a third emulsion, at the outlet of the mixer. Said third emulsion is chemically the same as the second emulsion, but it consists in monodisperse double droplets, whereas the second emulsion consisted in polydisperse double droplets. The third emulsion typically consists of a dispersion of double droplets comprising a core consisting of one or more single droplets of composition C1, and a layer of composition C2 surrounding said core, said double droplets being dispersed in composition C3.

The difference between the second emulsion and the third emulsion is the variance in size of the double droplets: the droplets of the second emulsion are polydisperse in size whereas the droplets of the third emulsion are monodisperse, thanks to the fragmentation mechanism described above.

Preferably, the second emulsion is introduced at the inlet of the mixer continuously, meaning that the amount of double emulsion introduced at the inlet of the mixer is the same as the amount of third emulsion outgoing from the outlet of the mixer.

When the double emulsion is in the gap between the two cylinders, the shear rate y applied to said emulsion is given by the following equation:

$$\gamma = \frac{R_i \omega}{(R_o - R_i)}$$

wherein $\omega$ is the angular velocity of the rotating inner cylinder, $R_o$ is the inner radius of the fixed outer cylinder, and $R_i$ is the outer radius of the rotating inner cylinder.

The parameters of the Couette-geometry mixer (i.e. the angular velocity and the gap between the cylinders) are tuned so that the shear rate y is from $1\,000\,s^{-1}$ to $20\,000\,s^{-1}$.

Since the size of the droplets of the third emulsion subsequently corresponds to the size of the solid microcapsules after polymerization, it is possible to tune the microcapsule size and shell thickness by adjusting the shear rate y during step c), with a strong correlation between decreasing droplet size and increasing shear rate.

This allows the resultant dimensions of the microcapsules to be tailored by varying either the angular velocity of the rotating cylinder, or the inner radius of the fixed outer cylinder, or both.

FIG. 1 schematically represents the method of the invention and notably schematically represents monodisperse droplets 10 obtained in step c).

Figure 2:
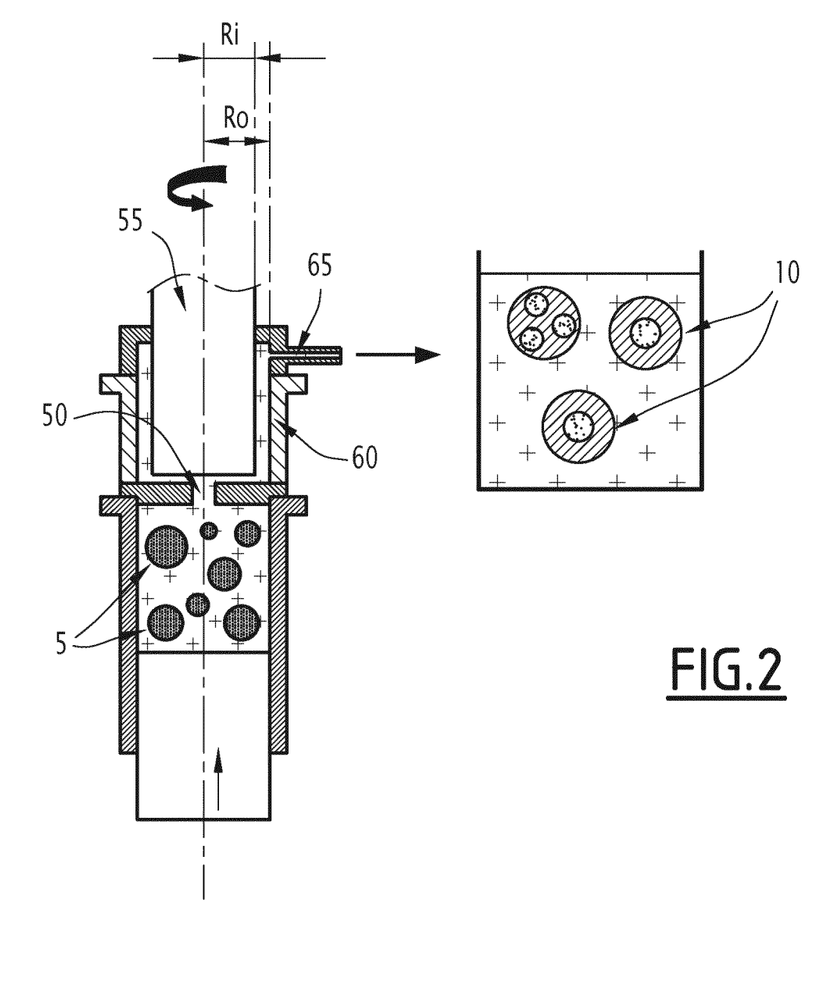
FIG. 2 schematically represents a Couette-geometry mixer.

FIG. 2 schematically represents a Couette-geometry mixer suitable for the preferred embodiment of the method of the invention and notably schematically represents the polydisperse droplets 5 of the second emulsion being introduced at the inlet 50, in the gap between the rotating inner cylinder 55 of outer radius $R_i$ and the fixed outer cylinder 60 of inner radius $R_o$, thus providing the monodisperse droplets 10 of third emulsion outgoing through the outlet 65.

Step d)

During step d), the double droplets of the third emulsion are cross-linked to provide microcapsules encapsulating the active material.

More particularly, the shell of these double droplets consisting of the cross-linkable composition C2 is cross-linked and thus converted into a viscoelastic polymeric shell matrix, encapsulating and protecting the active material from release in the absence of a mechanical trigger.

The mechanical properties of the polymerized shell of the microcapsules can be tailored by modifying the ratio of monomer or polymer to cross-linker within the initial composition C2.

The composition obtained after step d), comprising the microcapsules of the invention dispersed in composition C3, is ready-to-use and does not need to be washed or does not need any post-treatment.

The solid microcapsules obtained according to the method of the invention have an average diameter (as measured by image analysis of optical microscopy images or transmission electron microscopy images) preferably comprised from 0.1 μm to 10 μm, preferably from 0.2 μm to 5 μm.

The thickness of the polymerized shell of the solid microcapsules obtained according to the method of the invention is typically between 10 nm and 2.5 μm, preferably from 100 nm to 1 000 nm.

According to one embodiment, during step d), the cross-linking is carried out by submitting the double droplets obtained in step c) to a source of light, preferably a source of UV light, able to initiate the cross-linking of composition C2.

Preferably, the source of UV light emits in the range of 100 nm-400 nm.

The double droplets obtained in step c) are typically submitted to a source of light for 1 minute to 15 minutes.

According to this embodiment, the cross-linkable composition C2 is photocross-linkable and the polymerization is thus photo-initiated.

FIG. 1 schematically represents the method of the invention and notably schematically represents monodisperse polymerized microcapsules 20 obtained in step d), after polymerization of the shell of composition C2.

The method of the invention allows a great versatility and is thus suitable for the encapsulation of various active materials, independent of their viscosity or chemical properties.

The method of the invention allows the tailoring of the shell thickness and/or the size of the microcapsules by adjusting the ratio of composition C1 over composition C2 in step a), and/or the shear rate applied by the Couette-geometry mixer in step c).

The method of the invention allows the tailoring of the overall content of active material in the resulting composition obtained after step d), by adjusting the ratio of first emulsion over composition C3 in step b).

The method of the invention allows the tailoring of the mechanical susceptibility, the flexibility, and/or the brittleness of the solid microcapsules (particularly of the shell), by adjusting the content of cross-linker in composition C2.

Microcapsules and Composition

The method of the invention enables the preparation of solid microcapsules, comprising a core consisting of the composition C1 comprising an active material, said core being encapsulated by a solid (polymerized or cross-linked) shell of polymerized composition C2.

The core of the microcapsules may consist of a single droplet or several droplets of composition C1.

The core of the microcapsules may be a liquid solution, either aqueous or oily, a liquid/liquid emulsion, or a dispersion of (nano)particles in a liquid composition.

The microcapsules of the invention are dispersed in a continuous liquid composition C3.

The method of the invention enables the preparation of monodisperse solid microcapsules, thanks to the specific fragmentation mechanism described above in step c).

One object of the present invention is also a series of solid microcapsules, said microcapsules being obtainable by the method of the invention above-defined, each microcapsule comprising:

a core comprising a composition comprising at least one active material as defined above, and a solid cross-linked shell surrounding said core, wherein the standard deviation of microcapsule diameter distribution is below 25% or below 1 μm.

The series of solid microcapsules of the invention is a monodisperse population of microcapsules.

The population of microcapsules can be imaged with an optical microscope or transmission electron microscope and the subsequent images can be treated with an image analysis software in order to extract the distribution of microcapsule diameters and thus determine the monodispersity of the population of microcapsules.

Alternatively, techniques based on light scattering, sieving or centrifugation may be used.

According to one embodiment, the series of solid microcapsules of the invention has a standard deviation of microcapsule shell thickness distribution below 25% or below 300 nm.

According to one embodiment, the series of solid microcapsules is characterized in that the average diameter D of the solid microcapsules is less than or equal to 10 μm, preferably from 0.1 μm to 5 μm, more preferably from 0.3 μm to 1 μm.

According to one embodiment, the solid microcapsules of the invention are surfactant-free.

According to one embodiment, the solid microcapsules of the invention are water-free.

The method of the invention enables the preparation of such microcapsules, notably monodisperse microcapsules, having a mean size less than 10 μm.

The microcapsules of the invention, and the continuous phase in which they are dispersed, are advantageously free from any contaminant, such as surfactant, emulsifier, or unreacted monomers.

One object of the present invention is also a composition comprising a series of solid microcapsules as defined above, said microcapsules being dispersed in a continuous liquid phase.

Said continuous liquid phase typically corresponds to composition C3.

An object of the present invention is also a composition comprising a series of solid microcapsules according to the invention.

An object of the present invention is also a method for releasing an active material, comprising a step of applying a mechanical shear stress to a composition comprising a series of solid microcapsules as defined above.

EXAMPLES

Example 1—Versatility of the Encapsulation Method

The following materials were successfully used as composition C1:

| Material | Viscosity at 25° C. (mPa · s) |
|---|---|
| Polyalpha olefin (ExxonMobil PAO 100) | 2990 ± 44 |
| Polyalpha olefin (ExxonMobil PAO 40) | 892 ± 2 |
| Parrafin oil | 107 ± 1 |
| Mineral oil | 29 ± 0.2 |
| Hexadecane | 3.1 ± 0.1 |
| Water | 0.9 ± 0.1 |
| Toluene | 0.6 ± 0.1 |
| Wax (Gattefossé, Suppocire DM) | Not applicable (melting point = 40° C.) |

Composition C2 was made of:
89% CN981 (Sartomer, Arkema),
10% Hexanediol diacrylate,
1% Darocure 1173.
Composition C3 was ExxonMobil PAO 100.

Step a)

Composition C1 was added dropwise under constant mixing to composition C2 until a ratio C1:C2=1:4 was reached. After this step, an emulsion C1-in-C2 was formed.

Step b)

The C1-in-C2 emulsion was added dropwise under constant mixing to composition C3 until a ratio C1-in-C2:C3=1:4 was reached. After this step, a double emulsion C1-in-C2-in-C3 was formed.

Step c)

The double emulsion C1-in-C2-in-C3 was passed through a Couette-geometry mixer with a flowrate of 8 mL/min and rotation speed of 100 rpm, corresponding to a shear rate of 2 083 $s^{-1}$. After this step, a monodisperse double emulsion C1-in-C2-in-C3 was formed.

NB: for the wax, steps a), b) and c) were performed at 40° C.

Step d)

The resulting monodisperse double emulsion was submitted to UV irradiation to polymerize the microcapsules for 6 minutes using a Dymax Light Box ECE 2000 having an output light intensity of 0.1 W/$cm^2$ at 365 nm.

Images of the resulting solid microcapsules were obtained with a JEOL JEM 2010F transmission electron microscope and showed regular spherical shaped microcapsules.

This example illustrates that a variety of materials, having a wide range of viscosities and chemical properties, can be encapsulated according to the method of the invention.

Example 2—Robustness of the Encapsulation Method

An image analysis (using Image J software) was conducted on TEM pictures of microcapsules fabricated in Example 1. The results (average diameter and shell thickness of the microcapsule distributions, as well as standard deviations) are presented in the table below.

| Encapsulated material | Viscosity at 25° C. (mPa · s) | Capsule diameter (μm) | Shell thickness (μm) |
|---|---|---|---|
| ExxonMobil PAO 100 | 2990 ± 44 | 1.85 ± 0.6 | 0.32 |
| ExxonMobil PAO 40 | 892 ± 2 | 2.14 ± 0.87 | 0.38 |
| Parrafin oil | 107 ± 1 | 2.05 ± 0.96 | 0.41 |
| Mineral oil | 29 ± 0.2 | 2.1 ± 1 | 0.31 |
| Hexadecane | 3.1 ± 0.1 | 2.17 ± 1 | 0.29 |

This example illustrates that different materials can be encapsulated according to the invention with little variation of the microcapsule size and shell thickness.

Example 3—Full Containment of the Microcapsules

The two-component kit "Sylgard 184 silicon elastomer" commercialized by Dow Corning was used in this example. The two components, called A and B, are respectively a siloxane monomer composition and a siloxane cross-linking composition. When mixed together at a weight ratio A:B=10:1, these two components form a cross-linked solid elastomer within 24 hours at room temperature or within 2 hours at 90° C.

Encapsulation was carried out with component B as composition C1 and component A as composition C3.

Composition C2 was made of:
89% CN981 (Sartomer, Arkema)
10% Hexanediol diacrylate
1% Darocure 1173 (photoiniator)

Microcapsules Fabrication:

An overhead stirrer (Heidolph RZR 2021) equipped with a three-bladed propeller was used to fabricate the emulsions. Mixing speed was set to 1000 rpm. All steps were performed at room temperature.

Step a)

Composition C1 was added dropwise under constant mixing to composition C2 until a ratio C1:C2=1:6 was reached. After this step, an emulsion C1-in-C2 was formed.

Step b)

The C1-in-C2 emulsion was added dropwise under constant mixing to composition C3 until a ratio C1-in-C2:C3=1:4 was reached. After this step, a double emulsion C1-in-C2-in-C3 was formed.

Step c)

The double emulsion C1-in-C2-in-C3 was passed through a Couette-geometry mixer with a flowrate of 8 mL/min and rotation speed of 450 rpm corresponding to a shear rate of 9373 $s^{-1}$. After this step, a monodisperse double emulsion C1-in-C2-in-C3 was formed.

Step d)

The resulting monodisperse double emulsion was submitted to UV irradiation to polymerize the microcapsules for 6 minutes using a Dymax Light Box ECE 2000 having an output light intensity of 0.1 W/$cm^2$ at 365 nm.

The average diameter of the microcapsule distribution was 346 nm±80 nm and the average shell thickness of the microcapsule distribution was 62 nm±19 nm.

Microcapsules Stability:

The viscosity of the microcapsules dispersion resulting from step d) was measured at 25° C. with a rheometer HAAKE Rheostress™ 600 during 60 days.

No variation in viscosity was observed, demonstrating the absence of leakage of component B from the capsules.

Triggered Release:

After 60 days the solid microcapsules dispersion was sheared in a Couette-geometry mixer with a flowrate of 0.5 mL/min and rotation speed of 680 rpm corresponding to a shear rate of 17 200 s$^{-1}$, and then left at 90° C. for 2 hours.

It was then impossible to measure the viscosity of the sheared microcapsules dispersion because it had polymerized into a solid elastomer. This demonstrates that the capsules were ruptured under shear and had released their content.

This example demonstrates the fabrication of microcapsules containing a cross-linker and dispersed into a cross-linkable matrix. The resulting dispersion of microcapsules is stable for at least 60 days without polymerizing. Shearing this dispersion results in the rupture of microcapsules and triggers polymerization.

Example 4—Comparison of Different Methods—Characterization of the Monodispersity Solid microcapsules were prepared using the following compositions C1, C2, and C3:
Composition C1: ExxonMobil PAO40 (Polyalpha olefin with a viscosity of 892 mPa·s at 25° C.)
Composition C2:
89% CN981 (Sartomer, Arkema)
10% Hexanediol diacrylate
1% Darocure 1173 (photo-initiator)
Composition C3: ExxonMobil PAO100 (Polyalpha olefin with a viscosity of 2989 mPa·s at 25° C.)

An overhead stirrer (Heidolph RZR 2021) equipped with a three-bladed propeller was used to fabricate the emulsions. Mixing speed was set to 1 000 rpm. All steps were performed at 25° C.

Step a):
Composition C1 was added dropwise under constant mixing to composition C2 until a ratio C1:C2=1:4 was reached. After this step an emulsion C1-in-C2 was formed.

Step b):
The C1-in-C2 emulsion obtained after step a) was added dropwise under constant mixing to composition C3 until a ratio C1-in-C2:C3=1:4 was reached. After this step a double emulsion C1-in-C2-in-C3 was formed.

Mixing Step:
The double emulsion C1-in-C2-in-C3 was then sheared with different kinds of mixer:
an overhead stirrer (Heidolph RZR 2021) equipped with a three-bladed propeller with a mixing speed of 1 000 rpm,
an Ika T25 Ultra-Turrax mixer for 5 minutes at 24 000 rpm, or
a Couette-geometry mixer, with a flowrate of 8 mL/min and rotation speed of 450 rpm, corresponding to a shear rate of 9373 s$^{-1}$ (homogeneous high-shear mixing, corresponding to the conditions of step c) of the method of the invention).

Step d):
The emulsions were then submitted to UV irradiation to polymerize the microcapsules for 6 minutes using a Dymax Light Box ECE 2000 having an output light intensity of 0.1 W/cm$^2$ at 365 nm. The series of solid microcapsules thus obtained were subsequently imaged with an Olympus IX71 microscope equipped with a UPlanSApo 100×/1.4 objective and with a JEOL JEM 2010F transmission electron microscope. The resulting images were treated with Image J software to extract the distribution of capsule diameters.

Figure 3:
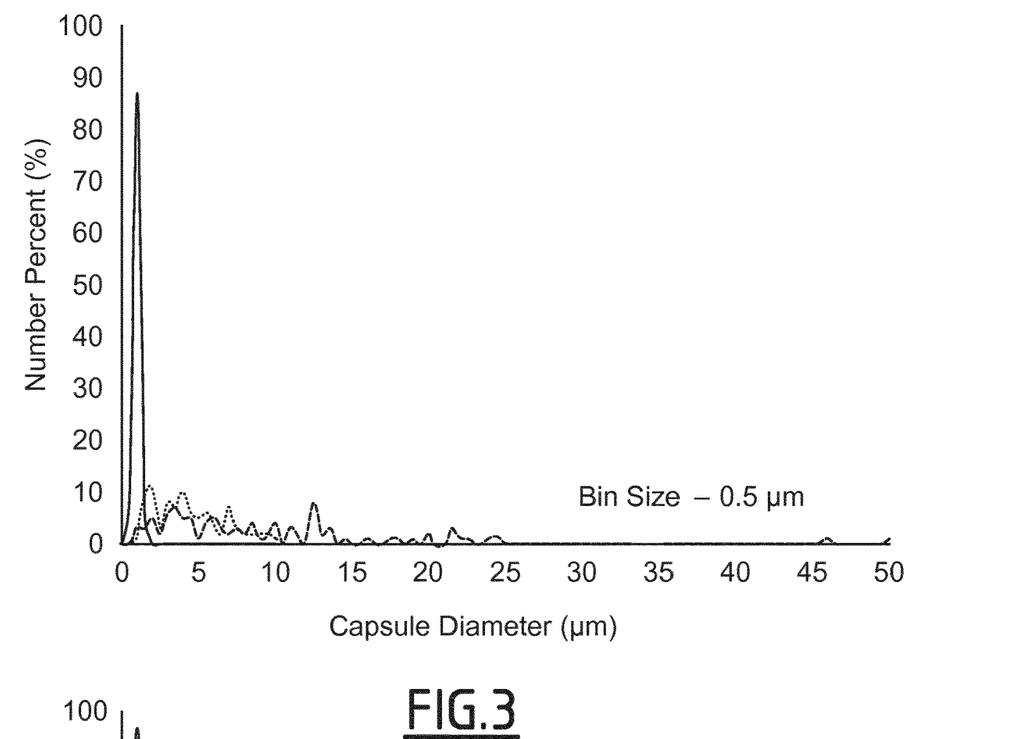
FIG. 3 illustrates a distribution of the series of capsules by capsule diameter distribution.
Figure 4:
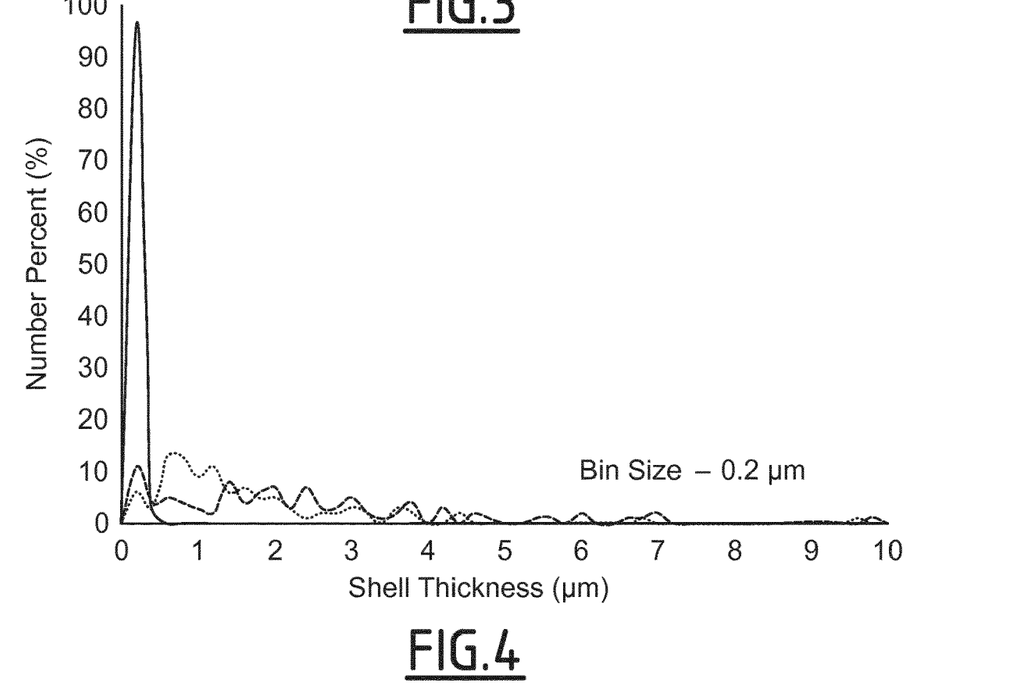
FIG. 4 illustrates a distribution of the series of capsules by shell thickness distribution.

The distribution of the series of capsules are represented in FIG. 3 (capsule diameter distribution) and FIG. 4 (shell thickness distribution), wherein the "- - -" plotline corresponds to the overhead stirrer, the " . . . " plotline corresponds to the Ultra-Turrax mixer, and the continuous plotline corresponds to the Couette-geometry mixer.

The series of solid microcapsules resulting from a mixing step carried out in an overhead stirrer (standard emulsification) has an average diameter is 9.05 μm and the standard deviation of the distribution is 8.16 μm or 90%. The average shell thickness is 2.32 μm and the standard deviation of the distribution is 2.01 μm or 87%.

This result illustrates the fact that standard mixers such yield solid capsules having very broad size distributions.

The series of solid microcapsules resulting from a mixing step carried out in Ika T25 Ultra-Turrax mixer, which provides heterogeneous high-shear mixing, has an average diameter of 5.18 μm and a standard deviation of 4.35 μm or 84%. The average shell thickness is 1.50 μm and the standard deviation of the distribution is 1.38 μm or 92%.

This result illustrates the fact that mixers such as the Ika T25 Ultra-Turrax allow decreasing the average size of the capsules, because of the high shear applied to the double emulsion, but still yield very broad size distributions.

By contrast, the series of solid microcapsules obtained according to the method of the invention, which results from a mixing step carried out in a Couette-geometry mixer, has an average diameter of 0.13 μm and a standard deviation of 0.03 μm or 23%.

This result demonstrates the relevance of the Couette-geometry mixer to obtain both small sizes of capsules and narrow distributions.

The invention claimed is:

1. Method for preparing solid microcapsules, comprising the steps of:
a) adding under agitation a composition C1 comprising at least one active material to a cross-linkable liquid composition C2,
wherein the active material is not an additive to be used in the lubricant, fuel or bitumen industries, or in drilling sludges or muds, or an additive to be used in oil exploration/production,
composition C1 and composition C2 being immiscible with each other,
so that a first emulsion is obtained, said first emulsion comprising droplets of composition C1 dispersed in composition C2,
b) adding under agitation the first emulsion obtained in step a) to a liquid composition C3,
composition C3 and composition C2 being immiscible with each other,
so that a second emulsion is obtained, said second emulsion comprising droplets dispersed in composition C3,
c) loading the second emulsion obtained in step b) in a mixer which applies a homogeneous controlled shear rate to said second emulsion, said shear rate being from 2 000 s$^{-1}$ to 100 000 s$^{-1}$,
so that a third emulsion is obtained, said third emulsion comprising droplets dispersed in composition C3, and
d) cross-linking the droplets obtained in step c),
so that solid microcapsules dispersed in composition C3 are obtained, wherein said method is carried out in the absence of surfactant and/or emulsifier.

2. The method according to claim 1, wherein the active material is solubilized into composition C1.

3. The method according to claim 1, wherein the active material is dispersed in the form of solid particles into composition C1.

4. The method of claim 1, wherein composition C2 comprises at least one monomer or polymer, at least one cross-linker and at least one initiator of polymerization.

5. The method of claim 1, wherein the viscosity of composition C2 at 25° C. is from 500 mPa·s to 100 000 mPa·s.

6. The method of claim 1, wherein the viscosity of composition C2 is higher than the viscosity of composition C1.

7. The method of claim 1, wherein during step a), the volume of composition C1 to the volume of composition C2 ratio is from 1:10 to 10:1.

8. The method of claim 1, wherein the viscosity of composition C3 at 25° C. is higher than the viscosity at 25° C. of the first emulsion obtained in step a).

9. The method of claim 1, wherein during step b), the volume of the first emulsion to the volume of composition C3 ratio is from 1:10 to 10:1.

10. The method of claim 1, wherein the mixer used in step c) is a Couette-geometry mixer, comprising two concentric cylinders, an outer cylinder of inner radius $R_o$ and an inner cylinder of outer radius $R_i$, the outer cylinder being fixed and the inner cylinder being rotating with an angular velocity $\omega$.

11. The method according to claim 10, wherein the angular velocity $\omega$ of the rotating inner cylinder is over than or equals to 30 rad·s$^{-1}$.

12. The method of claim 10, wherein the gap $d=R_o-R_i$ between the two concentric cylinders is from 50 μm to 1 000 μm.

13. The method of claim 1, wherein during step d), the cross-linking is carried out by submitting the droplets obtained in step c) to a source of light, able to initiate the cross-linking of composition C2.

14. A series of solid microcapsules, said microcapsules being obtained by the method of claim 1, each microcapsule comprising:
    a core comprising a composition comprising said at least one active material, and
    a solid cross-linked shell surrounding said core,
wherein the standard deviation of microcapsule diameter distribution is below 25% or below 1 μm.

15. The series of solid microcapsules according to claim 14, wherein the average diameter of the microcapsules is less than or equal to 10 μm.

16. The series of solid microcapsules of claim 14, wherein each microcapsule is surfactant-free.

17. The series of solid microcapsules of claim 14, wherein each microcapsule is water-free.

18. A composition comprising a series of solid microcapsules of claim 14.

19. A method for releasing an active material, comprising a step of applying a mechanical shear stress to a composition comprising the series of solid microcapsules of claim 14.

* * * * *